United States Patent
Lohwasser et al.

(10) Patent No.: US 11,440,876 B2
(45) Date of Patent: Sep. 13, 2022

(54) PROCESS TO PRODUCE A MONO VINYL THIOETHER

(71) Applicant: BASF SE, Ludwigshafen am Rhein (DE)

(72) Inventors: Ruth Lohwasser, Ludwigshafen (DE); Pavel Tuzina, Ludwigshafen (DE); Frank Bienewald, Ludwigshafen (DE); Dagmar Pascale Kunsmann-Keitel, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 17/607,017

(22) PCT Filed: Apr. 20, 2020

(86) PCT No.: PCT/EP2020/060947
§ 371 (c)(1),
(2) Date: Oct. 27, 2021

(87) PCT Pub. No.: WO2020/221607
PCT Pub. Date: Nov. 5, 2020

(65) Prior Publication Data
US 2022/0144767 A1   May 12, 2022

(30) Foreign Application Priority Data
Apr. 29, 2019 (EP) .................... 19171622

(51) Int. Cl.
*C07C 319/20* (2006.01)
(52) U.S. Cl.
CPC ................. *C07C 319/20* (2013.01)

(58) Field of Classification Search
CPC ................... C07C 319/18; C07C 319/20
See application file for complete search history.

(56) References Cited

U.S. PATENT DOCUMENTS

| 2,930,815 | A | * | 3/1960 | Nedwick | ............... | C07C 319/18 |
|---|---|---|---|---|---|---|
| | | | | | | 564/204 |
| 3,370,095 | A | * | 2/1968 | Vitcha | ................... | C07C 41/08 |
| | | | | | | 568/688 |
| 2003/0105354 | A1 | | 6/2003 | Pinkos et al. | | |

FOREIGN PATENT DOCUMENTS

SK            284667 B6 *  8/2005

OTHER PUBLICATIONS

International Search Report dated Jul. 21, 2020 in PCT/EP2020/060947, 3 pages.
Written Opinion dated Jul. 21, 2020 in PCT/EP2020/060947, 5 pages.
Atavin, et al., "Vinyl ethers containing tervalent phosphorus-II. New unsaturated phosphorous esters based on sulfur analogs of glycols", Journal of Organic Chemistry of the USSR, vol. 4, Issue 5, May 1968, pp. 765-768.

\* cited by examiner

*Primary Examiner* — Roaslynd A Keys
(74) *Attorney, Agent, or Firm* — Grüneberg and Myers PLLC

(57) ABSTRACT

A process produces a mono vinyl thioether by reacting acetylene with a compound containing one thiol group and one hydroxy group, referred to as a thiol-hydroxy compound, where the reaction is performed at a pressure below 2 bars.

10 Claims, No Drawings

PROCESS TO PRODUCE A MONO VINYL THIOETHER

CROSS-REFERENCE TO RELATED APPLICATIONS

This application is the National Stage entry under § 371 of International Application No. PCT/EP2020/060947, filed on Apr. 20, 2020, and which claims the benefit of priority to European Application No, 19171622.4, filed on Apr. 29, 2019. The content of each of these applications is hereby incorporated by reference in its entirety.

BACKGROUND OF THE INVENTION

Field of the Invention

The present invention relates to a process to produce a mono vinyl thioether by reacting acetylene with a compound comprising one thiol group and one hydroxy group, hereinafter referred to as thiol-hydroxy compound, wherein the reaction is performed at a pressure below 2 bars.

Description of Related Art

A well-known process for the synthesis of a vinyl ether is the Reppe process. According to the Reppe process a vinyl ether or vinyl thioether is obtained by reacting compounds with at least one hydroxy group or at least one thiol group with acetylene in presence of a basic catalyst. Such a process is described, for example, in US 2003/0105354. According to US 2003/0105354, the reaction is performed at a preferred range of pressure of 0.2 MPa to 2 MPa, corresponding to 2 to 20 bars. In the examples, the pressure is kept at 20 bars.

A. S. Atvin et al., Journal of Organic Chemistry of the USSR, volume 4, number 5 (May 1968), page 765 to 768, disclose a process for the preparation of 2-(vinylthio)ethanol which is performed at 11 gauge atm, which is an absolute pressure of 12 atm and corresponds to about 12 bars.

In case of compounds comprising both, hydroxy groups and thiol groups a mixture of various vinyl compounds is usually obtained, including thiol vinyl ether, hydroxy vinyl thioether and divinyl compounds.

For technical applications of vinyl compounds such mixtures have low suitability. Pure compounds are required for specific technical applications, such as polymerization processes.

For various technical applications, there is a demand in vinyl compounds with a thioether group and a free hydroxy group.

SUMMARY OF THE INVENTION

It was an object of this invention to provide an easy and economic process for the production of vinyl compounds with a thioether group and a free hydroxy group. Vinyl compounds with a thioether group and a hydroxy group shall be obtained in high yield and high selectivity by such process.

Hence, the process defined above has been found.

DETAILED DESCRIPTION OF THE INVENTION

The thiol-hydroxy compound is preferably a compound with a molecular weight below 1000 g/mol, more preferably below 500 g/mol most preferably below 200 g/mol.

In a particularly preferred embodiment, the thiol-hydroxy compound is liquid at 20° C. and 1 bar.

Preferred thiol-hydroxy compounds are compounds of formula I

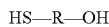

wherein R is a linear or branched aliphatic hydrocarbon group which may comprise oxygen in form of ether groups. Preferably, the linear or branched aliphatic hydrocarbon group comprises 1 to 10, more preferably 2 to 6, specifically 2 to 4 carbon atoms.

In a particularly preferred embodiment, R is ethylene, n-propylene or n-butylene.

In a most preferred embodiment, the compound of formula I is 2-hydroxy-ethan-1-thiol of formula

and the process is a process to produce vinyl thioethanol of formula

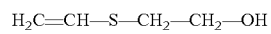

The reaction is preferably performed in presence of a catalyst. The catalyst is preferably an alkali salt of the thiol-hydroxy compound.

The alkali salt is preferably prepared by adding a metal hydroxide, preferably an alkali metal hydroxide, most preferably sodium or potassium hydroxide to the thiol-hydroxy compound and reacting the metal hydroxide with the thiol-hydroxy compound at elevated temperatures, for example at 50 to 150° C.

Preferably, the catalyst, respectively the alkali salt, is used in an amount of 0.1 to 10 parts by weight, more preferably of 0.5 to 7 parts by weight and most preferably of 1 to 5 parts by weight per 100 parts by weight of the thiol-hydroxy compound.

The alkali salt may be prepared separately or in-situ. In case of a separate preparation, the desired amount of alkali salt is prepared separately and is then is added to the reaction mixture. In case of an in-situ preparation, the alkali metal hydroxide is added to the reaction mixture in an amount to obtain the desired amount of alkali salt in situ under the conditions of the reaction.

The reaction may be performed in presence of a solvent. Usually a solvent is not required as the thiol-hydroxy compound used and the obtained mono vinyl thioether are preferably liquid themselves under the conditions of the reaction. More preferably, the thiol-hydroxy compound used and the obtained mono vinyl thioether are liquid at 20° C. and 1 bar.

The vinylation of thiol-hydroxy compound with acetylene is preferably performed at 50 to 200° C., notably at 80 to 150° C. and more preferably at 90 to 120° C.

The reaction is performed at a pressure below 2 bars, preferably at a pressure below 1.5 bars, more preferably at a pressure below 1.3 bars. In a preferred embodiment the pressure is at least 0.5 bars and more preferably at least 0.8 bars.

In a most preferred embodiment, the reaction is performed at a pressure of 0.8 to 1.3 bars, notably at a pressure of 0.9 to 1.1 bars and most preferably at 1 bar. The pressure may be the pressure of acetylene itself or of mixtures of acetylene with an inert gas, such as nitrogen. Preferably, acetylene is used not in combination with an inert gas and the above pressure is the acetylene pressure.

Preferably, the acetylene is fed directly into the liquid phase comprising the thiol-hydroxy compound and any products already formed. Notably, the acetylene may be introduced through the stirrer (in case of stirred tank reactors) or through nozzles directly into the liquid phase.

The process may be performed as batch process, semi-continuous process or continuous process. In a batch process all starting materials are added to the reactor before the reaction is started, in a semi-continuous process at least one of the starting materials is fed continuously during the reaction and in a continuous process all starting materials are fed continuously to the reactor and all products are withdrawn continuously from the reactor.

In a preferred embodiment, the process is performed semi-continuously or continuously.

In a preferred semi-continuous process, the whole amount of the thiol-hydroxy compound is added to the reactor whereas acetylene is fed continuously to the reactor during the reaction and unreacted acetylene as well as any other gaseous compounds are withdrawn from the reactor continuously while the pressure is kept below 2 bars, respectively below the preferred values or in the preferred ranges listed above.

The process may be performed in a single reactor or in several successive reactors, for example a reactor battery. Suitable reactors include stirred tank reactors, batteries of stirred tank reactors, flow tubes, bubble columns and loop reactors.

The reaction may be terminated, for example, by decreasing the temperature and/or stopping the acetylene feed.

The obtained product mixture comprises the mono vinyl thioether.

As by-product, it may comprise the divinyl compound resulting from the vinylation of the thiol group and the hydroxy group of the thiol-hydroxy compound. In case of 2-hydroxyethan-1-thiol as thiol-hydroxy compound, a divinyl compound of formula $$H_2C=CH-S-CH_2-CH_2-O-CH=CH_2$$

may be obtained as by-product.

The obtained product mixture may further comprise unreacted thiol-hydroxy compound.

Preferably, more then 90% by weight, notably more then 95% by weight and more preferably more the 98% by weight of the thiol-hydroxy compound are consumed in case of a batch or semi continuous process. A continuous process may preferably be operated with a steady state concentration of 10 to 80% by weight of the thiol-hydroxy compound in the reaction mixture.

It is an advantage of the invention that the formation of the divinyl compound is low. Preferably, the content of the divinyl compound is lower then 5% by weight, notably lower then 2% by weight and more preferably lower then 1% by weight based on 100% by weight of the mono vinyl thioether and the divinyl compound.

The catalyst, which is preferably an alkali salt, may be separated from the obtained product mixture by usual methods. Due to the high conversion of the thiol-hydroxy compound and the high selectivity, a further work-up of the product mixture obtained in a batch or semi-continuous process and removal of unconsumed thiol-hydroxy compound is usually not required. In a continuous process, unconsumed thiol-hydroxy compound may be separated from the product mixture and may be recycled to the reaction.

The mono vinyl thioether obtained may, for example, be purified by distillation.

The process of this invention is an easy and economic process to produce mono vinyl thioethers. The mono vinyl thioethers are obtained in high yields. The selectivity is very high. Only very low amounts of by-products such as divinyl compounds are formed. A separation of the low amounts of divinyl compounds from the product mixture obtained is usually not necessary.

EXAMPLES

Examples 1 to 4: Vinylation at Different Acetylene Pressures

A 0.3-liter autoclave was charged with 100 g of 2-mercaptoethanol (molecular weight: 78.13 g/mol) and 5 g of KOH pellets. The reactor was closed, heated to 100° C. and acetylene was passed through 6 norm-liters/hour under the pressure listed in table 1 for a reaction time of 10 hours. A norm-liter is one liter of a gas has at 0° C. and 1013 millibar. The composition of the mixture obtained in the reactor after 10 hours of reaction was analyzed via gas chromatography. The percentages listed in table 1 are area percentages of the corresponding peaks. The area percentages correspond substantially to the respective weight percentages. The remaining percentages to 100% correspond to unreacted starting materials.

TABLE 1 results of examples 1 to 4

| example | pressure bar | area % vinyl thioethanol in product mixture | area % divinyl compound in product mixture |
|---|---|---|---|
| 1 | 17 | 89.1 | 6.5 |
| 2 | 11 | 89.1 | 3.8 |
| 3 | 5 | 94.8 | 1.6 |
| 4 | 1 | 98.3 | 0.3 |

The invention claimed is:

1. A process to produce a mono vinyl thioether, the process comprising:
   reacting acetylene with a thiol-hydroxy compound comprising one thiol group and one hydroxy group,
   wherein the reaction is performed at a pressure below 2 bars.

2. The process according to claim 1, wherein the thiol-hydroxy compound is a compound of formula I:

HS—R—OH wherein R is a linear or branched aliphatic hydrocarbon group which may comprise oxygen in the form of ether groups.

3. The process according to claim 1, wherein the thiol-hydroxy compound is 2-hydroxy-ethane-1-thiol.

4. The process according to claim 1, wherein the process is a process to produce vinyl thioethanol of formula:

$$H_2C=CH-S-CH_2-CH_2-OH.$$

5. The process according to claim 1, wherein the reaction is performed in presence of a catalyst.

6. The process according to claim 5, wherein the catalyst is an alkali salt of the thiol-hydroxy compound.

7. The process according to claim 5, wherein the catalyst is used in an amount of 0.1 to 10 parts by weight per 100 parts by weight of the thiol-hydroxy compound.

8. The process according to claim 1, wherein the reaction is performed at a pressure below 1.5 bars.

9. The process according to claim 1, wherein the acetylene is fed directly into a liquid phase comprising the thiol-hydroxy compound and any products already formed.

10. The process according to claim 1, wherein the acetylene is fed continuously to a reactor and unreacted acetylene as well as any other gaseous compounds are withdrawn from the reactor while the pressure is kept below 2 bars.

\* \* \* \* \*